US006320935B1

(12) United States Patent
Shinar et al.

(10) Patent No.: US 6,320,935 B1
(45) Date of Patent: Nov. 20, 2001

(54) DOSIMETER FOR A MINIATURE ENERGY TRANSDUCER FOR EMITTING X-RAY RADIATION

(75) Inventors: Guy Shinar; Shmuel Bukshpan, both of Rehovot (IL)

(73) Assignee: X-Technologies, Ltd., Orangeburg, NY (US)

( * ) Notice: Subject to any disclaimer, the term of this patent is extended or adjusted under 35 U.S.C. 154(b) by 0 days.

(21) Appl. No.: 09/513,959

(22) Filed: Feb. 28, 2000

(51) Int. Cl.[7] ........................................... A61N 5/10
(52) U.S. Cl. ........................... 378/119; 378/121; 378/64; 378/65; 378/207
(58) Field of Search .............................. 378/64, 65, 119, 378/121, 207

(56) References Cited

U.S. PATENT DOCUMENTS

| Re. 34,421 | 10/1993 | Parker et al. ................ 378/121 |
|---|---|---|
| 3,777,124 | 12/1973 | Pavkovich ................ 600/1 |
| 4,976,266 | 12/1990 | Huffman et al. ................ 600/436 |
| 5,006,714 | * 4/1991 | Attix ................ 250/368 |
| 5,090,043 | 2/1992 | Parker et al. ................ 378/121 |
| 5,153,900 | 10/1992 | Nomikos et al. ................ 378/65 |
| 5,243,638 | 9/1993 | Wang et al. ................ 378/119 |
| 5,422,926 | 6/1995 | Smith et al. ................ 378/121 |
| 5,428,658 | 6/1995 | Oettinger et al. ................ 378/119 |
| 5,434,415 | * 7/1995 | Terada et al. ................ 250/368 |
| 5,528,652 | 6/1996 | Smith et al. ................ 378/65 |
| 5,547,454 | 8/1996 | Horn et al. ................ 600/1 |
| 5,566,221 | 10/1996 | Smith et al. ................ 378/145 |
| 5,583,908 | * 12/1996 | Antich et al. ................ 378/65 |
| 5,621,780 | 4/1997 | Smith et al. ................ 378/65 |
| 5,704,890 | * 1/1998 | Bliss et al. ................ 600/1 |
| 5,729,583 | 3/1998 | Tang et al. ................ 378/122 |
| 5,811,814 | * 9/1998 | Leone et al. ................ 250/368 |
| 5,854,822 | 12/1998 | Chornenky et al. ................ 378/122 |
| 5,905,262 | * 5/1999 | Spanswick ................ 250/368 |
| 5,910,102 | 6/1999 | Hastings ................ 600/3 |

(List continued on next page.)

FOREIGN PATENT DOCUMENTS

| 0 860 180 A2 | 8/1998 | (EP) . |
|---|---|---|
| 0 860 181 A2 | 8/1998 | (EP) . |
| 0 860 180 A3 | 4/1999 | (EP) . |
| 0 860 181 A3 | 4/1999 | (EP) . |
| WO 97/07740 | 3/1997 | (WO) . |
| WO 98/36796 | 8/1998 | (WO) . |
| WO 99/09580 | 2/1999 | (WO) . |
| WO 99/36938 | 7/1999 | (WO) . |
| WO 99/44687 | 9/1999 | (WO) . |
| WO 99/45562 | 9/1999 | (WO) . |
| WO 99/45563 | 9/1999 | (WO) . |

Primary Examiner—Robert H. Kim
Assistant Examiner—Allen C. Ho
(74) Attorney, Agent, or Firm—Rossi & Associates

(57) ABSTRACT

A dosimeter for an x-ray brachytherapy system permits in situ monitoring and control of radiation treatment via a miniaturized energy transducer within a human body. The dosimeter comprises a scintillating optical fiber having a distal end which is placed at the treatment site and a proximal end which is coupled to a dosimeter measurement unit. Utilizing energy supplied by an energy source, the miniaturized transducer generates x-ray photons. The scintillating optical fiber absorbs x-ray photons, converts the x-ray photons into light photons, and conveys the light photons to a dosimeter measurement unit. The light photons are converted into an electrical current which is representative of the intensity of the x-ray photons. The dosimeter measurement unit utilizes the electrical current to calculate and display the instantaneous and accumulated radiation dose, and radiation dose parameters are utilized to adjust energy levels, which are sent to the miniature energy transducer. Use of the miniaturized energy transducer in combination with the dosimeter eliminates most of the problems related to the methods based on the use of radioactive sources and offers a method for efficient, accurate, and controllable radiation treatment.

9 Claims, 2 Drawing Sheets

U.S. PATENT DOCUMENTS

| | | | |
|---|---|---|---|
| 5,984,853 | | 11/1999 | Smith .......................................... 600/1 |
| 6,069,938 | * | 5/2000 | Chornenky et al. ................. 378/122 |
| 6,087,666 | * | 7/2000 | Huston et al. .................... 250/484.5 |
| 6,140,651 | * | 10/2000 | Justus et al. .................... 250/390.11 |
| 6,148,061 | * | 11/2000 | Shefer et al. ........................ 378/121 |
| 6,195,411 | * | 2/2001 | Dinsmore ............................... 378/65 |
| 6,241,670 | * | 6/2001 | Nambu ................................. 600/427 |

* cited by examiner

DOSIMETER FOR A MINIATURE ENERGY TRANSDUCER FOR EMITTING X-RAY RADIATION

FIELD OF THE INVENTION

The present invention relates to an apparatus and method for providing x-ray brachytherapy treatment in humans. More specifically, the present invention relates a dosimetry system used in conjunction with a miniature x-ray emitting transducer, which measures a radiation dosage, displays an instantaneous and cumulative radiation dose, and adjusts the operating parameters of the x-ray emitting transducer during treatment via a control feedback loop.

BACKGROUND OF THE INVENTION

Restenosis is a heart condition that afflicts 35%–50% of all people who undergo balloon angioplasty to improve blood flow in narrowed sclerotic arteries. The condition consists of a significant re-closing of the treated artery segment hours to several months after the procedure. As a result, the arterial lumen size is decreased and the blood flow downstream from the lesion site is impaired. Consequently, patients afflicted with restenosis must undergo an additional balloon angioplasty, and in some cases a coronary bypass surgery must be performed. Aside from pain and suffering of these patients, recurrent stenosis imposes a serious economic burden on society, with estimated restenosis expenses as high as 3.0 billion dollars per year in the United States economy alone.

Attempts to treat restenosis have been concentrated in both the pharmacological and medical device areas. While pharmacological solutions have been proved effective in treating only acute restenosis, a condition developing immediately after balloon angioplasty, some progress has been made with medical devices in the treatment of long term restenosis, a condition developing after a few months following balloon angioplasty. Stents can be inserted into an occluded artery to hold it open. Stents may prevent two of the three mechanisms that cause recurrent stenosis, namely, elastic recoil of the artery and negative remodeling of the arterial structure. The third mechanism, neointimal growth, a proliferation of smooth muscle cells from the lesion into the lumen, is not prevented by stents.

Ionizing radiation holds great promise for treating restenosis. Ionizing radiation serves to damage undesirable hyper-proliferating tissue and ultimately to prevent the hyper-proliferation of cells in the irradiated region. Gamma and beta radiation delivered at the location of stenotic lesions effectively stop both animal and human intimal proliferation. The effective, yet non-hazardous, required dose to treat human restenosis is between seven and forty Gray (mjoule/gram), preferably a dosage greater than fifteen Gray, that penetrates the artery wall at a two mm depth over the lesion length.

Because of the promise that radiation holds for avoiding recurrent restenosis, many methods have been proposed to provide ionizing radiation treatment. These treatment methods may be grouped into three categories: conventional external x-ray irradiation; gamma and beta brachytherapy; and x-ray brachytherapy External x-ray irradiation cannot treat restenosis safely and effectively. The clinically required doses needed to successfully treat arterial lesions may damage the heart muscle and other organs, due to the non-localized nature of external x-rays. Conventional x-ray radiation for radiotherapy is produced by the following process. High energy electrons are generated and accelerated in a vacuum to impact on a metal target. The sudden deceleration of the high speed electrons into a solid target produces x-rays. Characteristic x-ray radiation results due to a process wherein the bombarding electron ionizes the atom it strikes by removing an electron from one of the atomic orbital shells, leaving a vacancy. An electron from a more remote atomic orbital shell fills this vacancy by jumping to the vacant atomic orbital shell. The consequent release of energy appears as an x-ray photon. Bremsstraalung x-ray radiation is the result of an interaction between a high speed electron and a nucleus. As the electron passes in the vicinity of a nucleus, it suffers a sudden deflection and acceleration. As a result, a part or all of its energy is dissociated from it and propagates in space as an x-ray photon. Conventional x-ray production tubes operate at high voltages, in the range of from 200 kV to 500 kV. However, appreciable x-rays may be produced in x-ray tubes having acceleration voltages as low as 20 kV. The x-ray emission is directly proportional to the electron beam current. However, the efficiency of x-ray generation is independent of electron current, but rather depends on the atomic number of the target material and on the acceleration voltage.

In gamma and beta brachytherapy, a radioactive source is introduced to the treatment site using a special radiation catheter, and the source is placed at this treatment site for a predetermined time, as to deliver the proper radiation dose. Presently, radiation catheters, based on the use of radioactive sources such as beta–emitting $^{32}$P, $^{90}$Sr/$^{90}$Y, $^{188}$W/$^{188}$Re, beta+emitting $^{48}$SV or gamma emitting $^{192}$Ir, are at various stages of development and clinical evaluation. Radioactive stents are also used as alternative delivering means, composed of the above radioactive isotopes.

The gamma and beta radioactive sources used by radiation catheters and radioactive stents have several drawbacks. Their ability to provide selective control of treatment time, radiation dosage, or radiation intensity is limited; and the handling of radioactive materials presents logistical, regulatory, and procedural difficulties. In addition, these devices jeopardize patients by exposing healthy organs to dangerous radiation during the introduction of the radiation source. Hospital personnel that handle radioactive materials are also at risk due to exposure. In addition to the risks these devices impose on patients, hospital staff, and the environment, use of these devices involves a regulatory burden due to the need to comply with nuclear regulatory requirements.

X-ray brachytherapy offers an alternative approach to providing ionizing radiation treatment. In x-ray brachytherapy an internal x-ray emitting miniature energy transducer generates x-rays in-situ. This system offers certain advantages with respect to intra vascular gamma and beta sources. These advantages are, but not limited to, localization of radiation to the treatment site so that the treatment site may be irradiated with minimal damage to surrounding healthy tissue; reduction of hospital personnel risk due to exposure to radioactive materials; and minimization of the regulatory burden that raises from the need to comply with nuclear regulatory requirements.

Another method for the production of x-rays that can possibly contribute to x-ray brachytherapy is direct conversion of light into x-ray radiation. The interaction of light with a target can produce highly energetic x-rays when the power densities achieved are in the range of $10^{16}$–$10^{17}$ watt/cm$^2$. With the development of the femtosecond laser, such power densities are achievable with moderate size lasers (See C. Tillman et al, NIMS in Phys. Res. A394

(1997), 387–396 and U.S. Pat. No. 5,606,588 issued to Umstadter et al., the contents of each of which are incorporated herein by reference). A 100 femtosecond, one mJ laser pulse focused down to a 3 micron spot, for example, will reach these power density levels.

A variety of medical applications of the direct laser light conversion method of x-ray generation are currently in the development stage. The direct laser light conversion method, for example, has been considered for medical imaging (See, Herrlin K et al. Radiology (USA), vol. 189, no. 1, pp. 65–8, October 1993). Another medical application of femtosecond lasers is in improved non-thermal ablation of neural or eye tissue for surgical purposes (See, F. H. Loesel et al. Appl.Phys.B 66, 121–128 (1998)). The development of compact table top models of femtosecond lasers makes laser generated x-rays an attractive alternative for radiotherapy.

Based on the above, an in-situ radiation treatment apparatus and method has been developed to emit a precisely controlled dose of radiation to a site within a patient's body, such as the interior of an arterial lesion. Co-pending and commonly assigned U.S. Pat. application Ser. No. 09/325,703 filed Jun. 3, 1999, and U.S. patent application Ser. No. 09/434,958 filed Nov. 5, 1999, the contents of which are incorporated herein by reference, describe miniaturized x-ray energy transducers that are coupled to flexible insertion devices to permit in-situ radiation treatment within a human body. The flexible insertion device incorporates optical fibers and/or electrical conductors to supply electrical and/or optical signals to the miniature energy transducer. The miniature energy transducer includes a cathode structure and anode structure spaced apart within a transducer body; and the cathode, anode, and transducer body form a sealed cavity. Electrons are accelerated from the cathode structure to the anode structure and are stopped by the anode to generate x-rays by the application of electrical pulses. The system is capable of delivering a therapeutic radiation dose greater than 15 Gray penetrating 2 mm into an artery wall, without utilizing radioactive materials.

A variety of different types of cathode and anode structures have been proposed for the miniature energy transducer. One proposal utilizes a hollow cathode that includes a cathode shell that defines a cavity. A laser light signal is introduced into the cavity in order to heat an outer surface of the cathode shell, thereby causing thermionic emission of electrons from the outer surface. Another proposal for a hollow cathode incorporates the use of an electron escape nozzle, wherein an electron plasma is generated in the cavity either by applying a light signal to an inner surface of the cathode shell or by providing a spark gap in the cavity of the conducting cathode shell. The electrons exit the cathode shell via the escape nozzle and are accelerated to the anode upon the application of a voltage pulse to the cathode. Still further, in a linear reverse cathode emission type of transducer, an anode is located at a first end of a transducer body and an emission element is located at a second end of the transducer body opposite the anode. The emission element is either a photo-emission electron source or a thermionic emission surface, and it generates electrons when activated by a light source or a high voltage source.

X-ray brachytherapy and radioactive brachytherapy have much in common. However, one main difference between x-ray and radioactive sources is the degree of confidence of the magnitude of the radiation dosage delivered to a treatment site within a patient. In radioactive brachytherapy, the level of activity of the radioactive source can be accurately measured prior to inserting the source into a patient. Once the source is inside the patient's body, it can be expected to maintain the same radiation characteristics during treatment with a very high degree of confidence. While radioactive brachytherapy devices outputs can be accurately predicted, on the other hand x-ray brachytherapy devices require independent verification of emission of radiation while they are operating inside a patient's body. Accordingly, regardless of the type of transducer which is utilized for x-ray brachytherapy, a dosimetry system is needed to measure the cumulative and instantaneous dose of radiation during treatment. PCT Patent Application WO99/45562 and PCT Patent Application WO99/45563 to Chomenky, et al. suggest a system that has a current integration device as a proxy for the dose imparted. The current measurement, however, cannot replace a direct measurement of the x-ray intensity, because x-rays produced are a function not only of the charge passing through the x-ray emitter, but also of the energy the charged electrons have when x-rays are produced. Even if the voltage across the x-ray tube is known, electrons may collide with the transducer walls or with ambient atoms, lose energy, and reach the anode where x-rays are produced with only a fraction of the energy that can be imparted by the voltage difference.

Accordingly, it is an object of the present invention to describe a miniature x-ray transducer with a dosimetry system that measures directly the x-ray intensity produced without relying on proxies such as current and voltage, which may give largely inaccurate results. Another object of the present invention is to provide a dosimetry system protected from electromagnetic noise and cross-talk with high voltages in the x-ray transducer. Furthermore, it is another object of the present invention to provide an energy transducer equipped with a dosimetry system wherein the most preferred embodiment of the dosimeter is as small as possible, so that measurement of the applied dosage may be located at a treatment site within a small blood vessel within the body. Still-further, it is another object of the present invention to provide a system which measures the imparted radiation dosage as a function of time, and then utilizes a feedback loop to enable accurate delivery of the desired dosing profile by controlled variation of the operating parameters of the x-ray transducer.

SUMMARY OF THE INVENTION

The invention provides an apparatus and method for a dosimeter for an x-ray brachytherapy system that permits in situ monitoring and control of radiation treatment via a miniaturized energy transducer within a human body. A miniature x-ray dosimeter measures a radiation dosage and adjusts the x-ray operating parameters during treatment via a control feedback loop. Use of the miniaturized energy transducer in combination with the dosimeter eliminates most of the problems related to the methods based on the use of radioactive sources and offers a method for efficient, accurate, and controllable radiation treatment. The flexible insertion device, miniature energy transducer, and dosimeter are dimensioned to provide access to very narrow blood vessels for x-ray radiation treatment.

An x-ray radiation treatment and dosimetry system comprises a flexible insertion device, an x-ray emitting energy transducer coupled to a distal end of the flexible insertion device, a dosimeter coupled to the x-ray emitting energy transducer, a device for providing energy to the energy transducer that generates x-rays, and a device for providing communication and feedback between the dosimeter and the energy providing device. The dosimeter comprises a scintillating optical fiber coupled to a dosimeter indicator and optionally a voltage probe and/or a current probe. The dosimeter indicator comprises a photo multiplier, a post processor, and a display device.

To generate x-ray and measure radiation dosage within a human body the following steps are followed. An x-ray transducer having a dosimeter is placed at a treatment area by manipulating a flexible insertion device attached to the x-ray energy transducer. A series of energy pulses are applied causing the x-ray transducer to generate electrons, accelerate the electrons towards an anode, and stop the electrons at the anode, thereby generating x-ray photons. Some of the x-ray photons are absorbed with the dosimeter, the x-ray photons are converted into light photons within the dosimeter, and the light photons are converted into an electrical current which is representative of the intensity of the x-ray photons. Next, the system utilizes the representative electrical current to calculate and display cumulative and instantaneous radiation dose parameters. A control system compares the measured dose to the pre-planned dose at a given time and decides, according to a predetermined algorithm, what the voltage, light source intensity (if a light source is used) and x-ray emitting tip location should be at the next instant. The control system also utilizes the accumulated radiation dose parameters to adjust the x-ray emitter operation parameters and pulses are repeated until the cumulative radiation dose equals a predetermined desired radiation dose.

Other advantages and features of the invention will become apparent from the following detailed description of the preferred embodiments and the accompanying drawings.

BRIEF DESCRIPTION OF THE DRAWINGS

The invention will now be described with reference to certain preferred embodiments thereof and the accompanying drawings, wherein.

DETAILED DESCRIPTION OF THE PREFERRED EMBODIMENTS

The present invention is particularly applicable to a dosimetry system for use during x-ray brachytherapy treatment of localized targets inside and outside the human body. Some therapeutic uses for the invention include computing cumulative and instantaneous radiation dosages to control the irradiation of coronary lesions to prevent restenosis and to treat tumors and arterio-venous malformations. It will be understood, however, that the invention is not limited to these particular applications.

Figure 1:
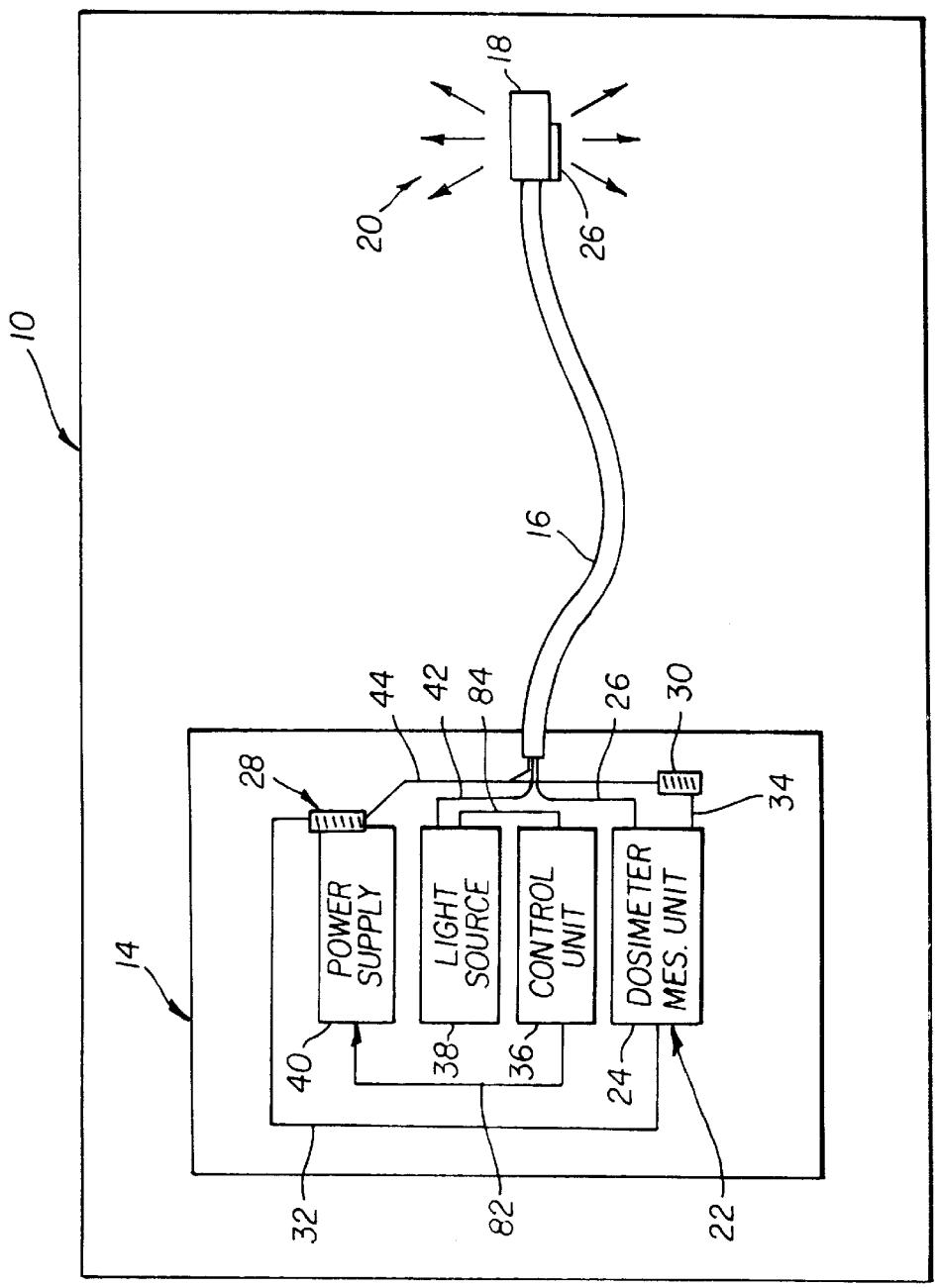
FIG. 1 is a functional block diagram of an x-ray brachytherapy system equipped with a dosimeter in accordance with the present invention.

FIG. 1 illustrates an x-ray brachytherapy system 10 in accordance with the present invention. The system 10 includes an energy source 14, a flexible insertion device 16 and a miniature energy transducer 18 located at a proximal end of the flexible insertion device 16. The flexible insertion device 16 contains means for supplying energy from the energy source 14 to the miniature energy transducer 18, which preferably converts electrical and/or optical signals received from the energy source 14 into x-ray radiation and distributes the x-ray photons (illustrated by arrows 20) in a predetermined distribution pattern. While the energy source 14 is located external to the patient, the flexible insertion device 16 is manipulated to place the miniature energy transducer 18 in an area to be treated within the body of a patient.

The miniature energy transducer 18 is preferably surrounded by x-ray transmissive insulation (not shown) that can be presented in direct contact with the human body. The transmissive insulation may be a material coated on an outer surface of the miniature energy transducer 18. Alternatively, the tralsmissive insulation may take the form of a capsule that encapsulates the miniature energy transducer 18. In any case, the miniature energy transducer 14 is preferably a relatively low-cost, replaceable and disposable unit. This avoids the necessity of complex sterilization processes required for instruments that are intended for multiple use.

The dosimeter system 22 comprises a dosimeter measurement unit 24 connected to a scintillating optical fiber 26. In a preferred embodiment, the scintillating optical fiber 26 is a standard plastic scintillating optical fiber, containing embedded dopant atoms which produce light photons upon being irradiated with x-ray photons. Such fibers are available from Bicron RMP of Solon, Ohio, a business unit of Saint Gobain Industrial Ceramics. The diameter of the optical fiber 26 preferably ranges from 0.01 mm to 1 mm. In a preferred embodiment, the system 22 includes a voltage probe 28 and a current probe 30 which are connected to the dosimeter indicator within the dosimeter measurement unit 24 with instrumentation electrical conductors 32, 34 respectively. The distal end of the scintillating optical fiber 26 is located in the immediate vicinity of the miniaturized energy transducer 18. Preferably, the bulk of the length of the scintillating optical fiber 26 is housed within the flexible insertion device 16. The dosimeter measurement unit 24 is preferably housed within the energy source 14, and it is connected to a control unit 36, which is also housed within the energy source 14.

In general, the energy source 14 is adapted to provide electrical and/or optical signals through the flexible insertion device 16 that is correspondingly configured to deliver the energy to the miniature energy transducer 18. Accordingly, the energy source 14 is provided with a power supply 40, such as voltage pulse generator, and an optional light source 38, for example a laser, respectively connected through an electrical conductor 44, preferably a coaxial cable, and an optical conductor 42 to the flexible insertion device 16. The control unit 36 directs the energy source 14 to deliver electrical and/or optical signals through the flexible insertion device 16 to the miniature energy transducer 18 according to the radiation dose profile required by the operator. During x-ray treatment, the control unit 36 also receives information regarding cumulative and instantaneous radiation dosage from the dosimeter measurement unit 24 and uses this information to achieve the required dosage amount of radiation. Optionally, control unit 36 can receive additional information from current probe 30 and voltage probe 28. The control unit 36 is connected to the power supply 40 and/or to the light source 38 with instrumentation electrical conductors 82 and 84 respectively so that the duration and amplitude of the energy supplied by the power supply 40 and/or the light source 38, as wells as the total treatment time, may be varied to control the distribution of the x-ray radiation produced by the miniature energy transducer 18.

Figure 2:
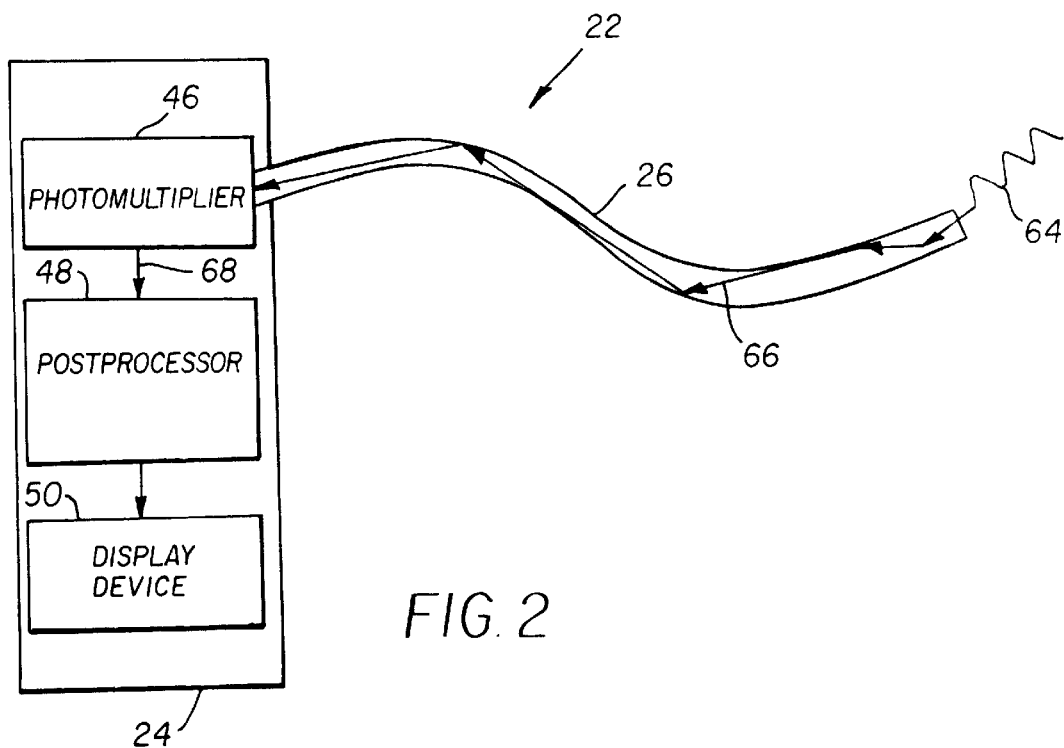
FIG. 2 is a functional block diagram of a dosimeter system.

FIG. 2 is a functional block diagram of the dosimeter system 22, in accordance with a preferred embodiment. The dosimeter measurement unit 24 contains a photo-multiplier 46, a post processor 48, and a display device 50. The proximal end of the scintillating optical fiber 26 is connected to the photo-multiplier 46, and the distal end of the scintillating optical fiber 26 is located adjacent to or inside the miniature energy transducer 18. The distal end of the scintillating fiber is shielded from non-x-ray radiation sources, such as UV light and ambient visible light, by a coating or a cover made out of aluminum foil for example. In a preferred embodiment, the post-processor 48 is an amplifier, and in another preferred embodiment the post-processor 48 is a photon counter. The post-processor 48 may also utilize a current measurement device or a microcomputer to process the output from the photo multiplier 46. The display device 50 is connected to the post processor 48.

Figure 3:
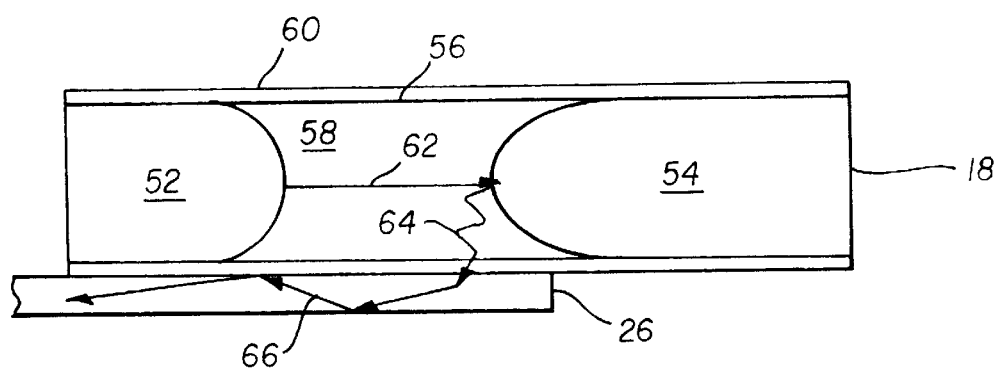
FIG. 3 is a cross-sectional view of a miniaturized energy transducer with a scintillating optical fiber.

FIG. 3 describes a preferred embodiment of the dosimeter system 22 wherein the distal tip of the scintillating optical fiber 26 is located directly adjacent to and in contact with the energy transducer 18, so that the scintillating optical fiber 26 receives the same initial x-ray intensity as the tissue which is being treated within a patient's body. The miniature energy transducer 18 includes a conducting cathode 52 and a conducting anode 54 respectively located at a proximal end and a distal end of an electrically insulating tube 56. The electrically insulating tube 56 is sealed and it is preferably 3–9 mm in length and less than 1.7 mm in diameter, and holds a vacuum within a hollow chamber 58 that typically varies from $10^{-2}$ to $10^{-9}$ Torr, depending on the type of electron generation method employed. The proximal end of the miniature energy transducer 18 is coupled to the flexible insertion device 16, which includes conductors that provide electrical and/or optical signals to the conducting cathode 52 as will be described in greater detail. In order for an electrical connection to be provided to the conducting anode 54 at the distal end of the miniature energy transducer 18, an outer conductive layer 60 is provided on the outer surface of the electrically insulating tube 56, which connects with a conductor provided in the flexible insertion device 16.

In another preferred embodiment (not shown) the miniature energy transducer 18 includes a conducting anode and a conducting cathode respectively located at a proximal end and a distal end of an electrically insulating tube. The electrically insulation tube is sealed and it is preferably 3–9 mm in length and less than 1.7 mm in diameter, and holds a vacuum within a hollow chamber that typically varies from $10^{-2}$ to $10^{-9}$ Torr, depending on the type of electron generation method employed. The proximal end of the miniature energy transducer 18 is coupled to the flexible insertion device 16, which includes conductors that provide electrical signals and/or an optical source to the conducting anode. In order for an electrical connection to be provided to the conducting cathode at the distal end of the miniature energy transducer 18, an outer conductive layer is provided on the outer surface of the electrically insulating tube, which connects with a conductor provided in the flexible insertion device 16.

In operation, electrons are generated at the conducting cathode 52 upon the application of an energy signal received from the energy source 14 while the conducting anode 54 is held at ground potential. Electron generation at the cathode generally takes between fractions of a nanosecond up to about one millisecond, depending on the electron generation method employed, during which time or immediately thereafter, a negative high-voltage electron accelerating pulse is introduced to the conducting cathode 52. The application of the voltage pulse to the conducting cathode 52, accelerates the electrons 62 generated at the conducting cathode 52 until they are stopped by the conducting anode 54, resulting in the generation of x-ray photons 64 at the anode 54. The conducting anode 54 and the conducting cathode 52 are held at ground potential once the pulse applied to the conducting cathode 52 terminates. The process is then repeated until the desired radiation dosage is achieved.

In another preferred embodiment (not shown), wherein the miniature energy transducer 18 includes a conducting anode and a conducting cathode respectively located at a proximal end and a distal end of an electrically insulating tube, the cathode is held at ground potential. In operation, electrons are generated at the conducting cathode, a process that generally takes between fractions of a nanosecond up to about one millisecond, depending on the electron generation method employed. During this period, or immediately thereafter, a positive high-voltage electron accelerating pulse is introduced to the conducting anode. The application of the voltage pulse to the conducting anode accelerates the electrons generated at the conducting cathode until they are stopped by the conducting anode, resulting in the generation of x-ray photons at the anode. The conducting anode and the conducting cathode are held at ground potential once the pulse applied to the conducting anode terminates. The process is then repeated until the desired radiation dosage is achieved. The miniature energy transducer 18 may be operated using direct current constant voltage as well.

Radiation dosage treatment parameters for x-ray brachytherapy are determined by a physician, and these treatment parameters are input into the control unit 36. The control unit 36 directs the power supply 40 and/or the light source 38 to send the required electric and light signals respectively via the flexible insertion device 16 to the miniature energy transducer 18. X-ray photons 64 emitted from the conducting anode 54 are absorbed by the scintillating optical fiber 26 at the treatment site, adjacent to the miniaturized energy transducer 18. The x-ray photons 64 interact with dopant atoms in the scintillating optical fiber 26 to induce light photons 66. The light photons 66 are channeled through the scintillating optical fiber 26 into the photo multiplier 46 as illustrated in FIG. 2. The photo multiplier 46 converts the light photons 66 into electrical current 68. The intensity of the induced light photons 66 is translated by the photo multiplier 46 into a representative electrical current 68. The photo multiplier 46 sends its output electrical current 68 to the post-processor 48 which translates the input signal into a corresponding dose rate occurring in-situ at the treatment site. The post-processor 48 may utilize a current measurement device or a microcomputer to ultimately calculate instantaneous and cumulative dosing parameters during radiation treatment. The dosing parameters are displayed at the display device 50, and this information is also fed back into the control unit 36, facilitating control by the operator.

In a preferred embodiment, a current probe 30 is also used. The current probe 30 is connected to the dosimeter measurement unit. It measures the electrical current levels across the x-ray tube and sends these parameters back to the control unit 36. In another preferred embodiment, a voltage probe 28 is also used. The voltage probe 28 measures the voltage levels of the power supply and sends these parameters back to the control unit 36.

EXAMPLE

In this example the operation of the system is demonstrated in accordance with a preferred embodiment. X-ray photons are emitted from a theoretical source. The x-ray are absorbed by a scintillating optical fiber and converted to light photons, which in turn are absorbed and attenuated within the scintillating optical fiber. Therefore, in calculating the radiation dose at the miniaturized x-ray transducer, the quantity of light photons arriving at the photo multiplier must be adjusted for this absorption and attenuation. This translation process requires the consideration of the following factors: the portion of the x-ray spectrum which is absorbed by the miniature energy transducer itself, the x-ray absorption coefficients of the scintillating optical fiber at different wavelengths, the number of light photons produced by one absorbed x-ray photon of specific wavelength, the optical fiber's capture rate which is a ratio of the quantity of light photons transmitted to the photo multiplier divided by the initial quantity of light photons produced at the distal edge of the scintillating optical fiber, adjacent to the x-ray transducer, and the quantity of current output by the photo multiplier in response to the input x-ray induced light photons. In addition, the output current of the post-processor must be calibrated due to the inherent characteristics of the post-processor itself.

The following treatment conditions are assumed: The x-ray source is a point source emitting $10^9$ x-ray photons per pulse, and the pulse length is 30 nsec. The optical fiber is located adjacent to the external wall of the source and 1.5 mm radially from the source. The optical fiber has a square cross-section with 0.2 mm diameter. The effective x-ray detection area, where x-ray photons may be absorbed is one mm long and 0.2 mm wide. Therefore, the effective detection area is:

$$A_d = 1 \text{ mm} * 0.2 \text{ mm} = 0.2 \text{ mm}^2$$

The x-ray source is located 1.5 mm from the scintillating optical fiber. Thus, the area of a 1.5 mm diameter spherical radiation shell created by the miniature energy transducer is:

$$A_s = 4*\pi*0.75^2 \text{ mm}^2 = 8 \text{ mm}^2$$

The number of photons striking the detecting area of the fiber is:

$$N_o = (A_d/A_s) \times 10^9 \text{ photons/pulse} \approx 3 \times 10^7 \text{ photons/pulse}$$

Table 1 describes the spectral and absorption characteristics of x-ray photons within a plastic scintillator target, which is assumed to represent the absorption characteristics of a preferred embodiment of the scintillating optical fiber. It is also assumed that the photon energy of all of the x-ray photons is in the 10 KeV–20 KeV range.

TABLE 1

| X-ray photon energy (KeV) | Approximate number of photons/ 25 kV voltage pulse difference across the x-ray tube | Mass attenuation coefficient (cm$^2$/gr) | Density (gr/cm$^3$) | Absorption length (mm) | Fraction of x-rays passing through the detector without being absorbed |
|---|---|---|---|---|---|
| 10 | $9 \times 10^6$ | 2.2 | 1 | 4.5 | $4 \times 10^{-2}$ |
| 15 | $1.2 \times 10^7$ | 0.77 | 1 | 13 | $1 \times 10^{-2}$ |
| 20 | $9 \times 10^6$ | 0.43 | 1 | 23 | $9 \times 10^{-3}$ |

The capture rate of the detector is 2%. The 1/e attenuation length is 2 m, and the length of the fiber is assumed to be 2 m. Eight thousand light photons are produced per MeV of absorbed x-ray energy. As a result, the number of photons that reach the photo multiplier per pulse is:

$$N_p = [9 \times 10^6 \times 4 \times 10^{-2} \times 80 + 1.2 \times 10^7 \times 1 \times 10^{-2} \times 120 + 9 \times 10^6 \times 9 \times 10^{-3} \times 160]$$

light photons/x-ray photon $\times 0.02 \times (1/e)$ light photons $= 0.4 \times 10^6$ light photons It is assumed that the photo multiplier has quantum efficiency of 20%, and that the photo multiplier gain is $10^6$. Therefore, the charge output is:

$$Q = 0.4 \times 10^6 \times 0.2 \times 10^6 \times 1.6 \times 10^{-19} = 1.3 \times 10^{-8} \text{ coulomb}.$$

It is assumed that the pulse length is 30 nsec. Therefore, the average current output by the photo multiplier during a pulse is:

$$I = 1.3 \times 10^{-8}/30 \times 10^{-9} = 0.4 \text{ amp}.$$

As a result, this signal can be easily detected over the typical noise level of 0.1 amps.

As can be seen by the illustrated examples, the dosimeter facilitates accurate control of radiation dosage during x-ray brachytherapy, by measuring the radiation dose as it occurs at the treatment site, adjacent to the miniature energy transducer. Further, the flexible insertion device not only serves the purpose of inserting and extracting the miniature energy transducer into and out of a patient's body, but also is required to supply the required high voltage pulses from the power supply and transmit dosimetry information via a scintillating optical fiber. Still further, the dosimetry system does not involve electrical currents inside the body. It is therefore decoupled from the high voltage lines that transmit electrical signals from the power supply source to the x-ray emitter. Dose measurement errors due to electrical cross-talk are therefore eliminated. The total diameter of the miniaturized transducer plus the scintillating optical fiber is preferably less than 2.5 mm thereby allowing the flexible insertion device to follow the contours of a blood vessel or any other body cavity.

Another advantage of the in-situ dosimeter is that its position is fixed with respect to the miniature x-ray emitter. Therefore, the dose measurement is independent of the specific location and orientation of the miniature x-ray emitter in the body.

The invention has been described with reference to certain preferred embodiments thereof. It will be understood, however, that modification and variations are possible within the scope of the appended claims. For example, other types of optical scintillating fibers may be utilized, and other signal processing devices may be incorporated into the post processor to process the output from the photo multiplier. Additionally, the dosimeter may be employed in non-x-ray brachytherapy systems to provide accurate in-situ measurement of dose and dose rate.

What is claimed is:

1. An x-ray transducer comprising:
    a scintillating optical fiber having a proximal end and a distal end;
    an insulating transducer body attached to the distal end of the scintillating optical fiber; and
    a dosimeter measuring unit coupled to the proximal end of the scintillating optical fiber.

2. An x-ray transducer as claimed in claim 1, wherein a longitudinal axis of the transducer body is parallel to the scintillating optical fiber and a total outer diameter measured perpendicular to the longitudinal axis of the x-ray transducer body and the optical fiber is less than 2.5 mm.

3. An x-ray radiation treatment system comprising:
    a flexible insertion device;
    an x-ray emitting energy transducer coupled to a distal end of the flexible insertion device;
    an energy source coupled to a proximal end of the flexible insertion device;

a dosimetry system that measures the output of the x-ray emitting energy transducer; and a control unit for controlling the amount of energy supplied by the energy source to the energy transducer in response to the output measured by the dosimetry system;

wherein the dosimeter system comprises a scintillating optical fiber coupled to the x-ray emitting energy transducer and a dosimeter measurement unit.

4. An x-ray radiation treatment system as claimed in claim 3, wherein the dosimeter system further comprises a voltage probe coupled to the dosimeter measurement unit.

5. An x-ray radiation treatment system as claimed in claim 3, wherein the dosimeter system further comprises a current probe coupled to the dosimeter measurement unit.

6. An x-ray radiation treatment system as claimed in claim 3, wherein the dosimeter measurement unit comprises a photo multiplier, a post processor, and a display device.

7. An x-ray radiation treatment system as claimed in claim 6, wherein the post processor comprises at least one of a microcomputer and a current measurement device.

8. An x-ray radiation treatment system as claimed in claim 3, wherein the energy source includes a pulsed voltage power supply that is coupled to the energy transducer by an electrical conductor provided in the flexible insertion device.

9. An x-ray radiation treatment system as claimed in claim 3, wherein the energy source includes a light source that is coupled to the energy transducer by an optical conductor provided in the flexible insertion device.

* * * * *